(12) United States Patent
Govari

(10) Patent No.: US 10,582,869 B2
(45) Date of Patent: Mar. 10, 2020

(54) CONNECTION OF ELECTRODES TO WIRES COILED ON A CORE

(71) Applicant: BIOSENSE WEBSTER (ISRAEL) LTD., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 795 days.

(21) Appl. No.: 14/063,477

(22) Filed: Oct. 25, 2013

(65) Prior Publication Data

US 2014/0305699 A1 Oct. 16, 2014

Related U.S. Application Data

(63) Continuation-in-part of application No. 13/860,921, filed on Apr. 11, 2013.

(51) Int. Cl.
*A61B 5/042* (2006.01)
*A61B 18/14* (2006.01)
(Continued)

(52) U.S. Cl.
CPC .......... *A61B 5/0422* (2013.01); *A61B 5/6858* (2013.01); *A61B 18/1492* (2013.01); *A61N 1/05* (2013.01); *A61N 1/056* (2013.01); *G02B 6/04* (2013.01); *G02B 6/449* (2013.01); *H01B 7/009* (2013.01); *H01B 13/0036* (2013.01); *H01B 13/06* (2013.01); *A61B 2017/00526* (2013.01); *A61B 2018/0016* (2013.01);
(Continued)

(58) Field of Classification Search
CPC .. A61B 18/1492; A61B 5/6858; H01B 7/009; A61N 1/05; A61N 1/056

USPC ............................................ 600/373; 29/825
See application file for complete search history.

(56) References Cited

U.S. PATENT DOCUMENTS 4,280,511 A * 7/1981 O'Neill .................. A61N 1/056
607/122
4,437,474 A * 3/1984 Peers-Trevarton .... A61N 1/056
29/605

(Continued)

FOREIGN PATENT DOCUMENTS

CN 101888812 11/2010
EP 0 617 916 A1 10/1994
(Continued)

OTHER PUBLICATIONS

U.S. Appl. No. 13/860,921, filed Apr. 11, 2013.
(Continued)

*Primary Examiner* — Lee S Cohen
*Assistant Examiner* — Erin M Cardinal
(74) *Attorney, Agent, or Firm* — Dergosits & Noah LLP; Todd A. Noah

(57) ABSTRACT

A method for attaching an electrode to cabling, including providing a cable having a plurality of insulated wires coiled around a central core. The method further includes removing insulation from each wire in a set of the coiled wires so as to provide a respective access channel to a respective section of a respective conductor of each wire in the set while the respective section remains coiled on the central core. The method further includes fastening a respective electrode to the respective access channel while the respective section remains coiled on the central core.

12 Claims, 6 Drawing Sheets

(51) Int. Cl.
| | |
|---|---|
| *A61N 1/05* | (2006.01) |
| *A61M 25/16* | (2006.01) |
| *A61B 5/00* | (2006.01) |
| *H01B 7/00* | (2006.01) |
| *H01B 13/06* | (2006.01) |
| *G02B 6/04* | (2006.01) |
| *G02B 6/44* | (2006.01) |
| *H01B 13/00* | (2006.01) |
| *A61B 18/00* | (2006.01) |
| *A61B 17/00* | (2006.01) |

(52) U.S. Cl.
CPC ............... *A61B 2018/00178* (2013.01); *A61B 2018/00267* (2013.01); *A61B 2562/125* (2013.01); *A61B 2562/222* (2013.01); *Y10T 29/49169* (2015.01); *Y10T 29/49174* (2015.01); *Y10T 29/49801* (2015.01)

(56) References Cited

U.S. PATENT DOCUMENTS

| | | | |
|---|---|---|---|
| 4,630,611 A * | 12/1986 | King | A61B 5/076 600/377 |
| 5,016,646 A * | 5/1991 | Gotthardt | A61N 1/056 607/122 |
| 5,391,199 A | 2/1995 | Ben-Haim | |
| 5,439,485 A | 8/1995 | Mar | |
| 5,476,495 A | 12/1995 | Kordis et al. | |
| 5,555,618 A * | 9/1996 | Winkler | A61B 5/0422 29/825 |
| 5,591,142 A * | 1/1997 | Van Erp | A61B 5/6852 604/264 |
| 5,755,687 A | 5/1998 | Donlon | |
| 5,772,590 A | 6/1998 | Webster, Jr. | |
| 5,796,044 A * | 8/1998 | Cobian | A61N 1/056 174/103 |
| 5,836,946 A | 11/1998 | Diaz | |
| 5,911,739 A | 6/1999 | Kordis et al. | |
| 6,004,269 A | 12/1999 | Crowley et al. | |
| 6,064,905 A | 5/2000 | Webster, Jr. et al. | |
| 6,213,995 B1 | 4/2001 | Steen et al. | |
| 6,239,724 B1 | 5/2001 | Doron et al. | |
| 6,289,250 B1 | 9/2001 | Tsuboi | |
| 6,332,089 B1 | 12/2001 | Acker et al. | |
| 6,400,981 B1 | 6/2002 | Govari | |
| 6,484,118 B1 | 11/2002 | Govari | |
| 6,584,345 B2 | 6/2003 | Govari | |
| 6,618,612 B1 | 9/2003 | Acker et al. | |
| 6,690,963 B2 | 2/2004 | Ben-Haim et al. | |
| 6,748,255 B2 | 6/2004 | Fuimaono et al. | |
| 6,973,340 B2 | 12/2005 | Fuimaono et al. | |
| 7,149,585 B2 * | 12/2006 | Wessman | A61N 1/05 219/522 |
| 7,229,437 B2 | 6/2007 | Johnson | |
| 7,239,922 B1 * | 7/2007 | Boogaard | A61N 1/0551 607/116 |
| 2002/0022782 A1 * | 2/2002 | Kiepen | A61B 5/0215 600/486 |
| 2002/0038139 A1 * | 3/2002 | Wessman | A61N 1/05 607/122 |
| 2002/0065455 A1 | 5/2002 | Ben-Haim et al. | |
| 2002/0143377 A1 * | 10/2002 | Wessman | A61N 1/05 607/116 |
| 2003/0092303 A1 | 5/2003 | Osypka | |
| 2003/0120150 A1 | 6/2003 | Govari | |
| 2004/0059404 A1 | 3/2004 | Bjorklund et al. | |
| 2004/0068178 A1 | 4/2004 | Govari | |
| 2006/0009404 A1 | 1/2006 | Williams | |
| 2010/0211147 A1 * | 8/2010 | Schiefer | A61N 1/05 607/116 |
| 2011/0137382 A1 * | 6/2011 | Swanson | A61N 1/0553 607/72 |
| 2012/0172714 A1 | 7/2012 | Govari | |
| 2012/0172717 A1 * | 7/2012 | Gonda | A61B 5/042 600/424 |
| 2012/0271135 A1 | 10/2012 | Burke et al. | |
| 2012/0271385 A1 | 10/2012 | Bernard | |
| 2012/0323089 A1 * | 12/2012 | Feer | A61B 5/01 600/301 |
| 2013/0150808 A1 * | 6/2013 | Ogle | A61M 25/0012 604/264 |
| 2013/0197616 A1 * | 8/2013 | Dollimer | A61N 1/05 607/116 |
| 2014/0309512 A1 | 10/2014 | Govari et al. | |
| 2016/0183877 A1 | 6/2016 | Williams et al. | |

FOREIGN PATENT DOCUMENTS

| | | |
|---|---|---|
| EP | 1723981 B1 | 8/2010 |
| EP | 2471480 A1 | 7/2012 |
| JP | S57128805 U | 8/1982 |
| JP | H08511438 | 12/1996 |
| JP | H10510731 | 10/1998 |
| JP | 2004130114 | 4/2004 |
| JP | 2010057943 | 3/2010 |
| JP | 2012510831 | 5/2012 |
| WO | 96/05758 A1 | 2/1996 |
| WO | 96/05768 | 2/1996 |
| WO | WO 00/62851 A1 | 10/2000 |
| WO | WO 2009/072039 A2 | 6/2009 |
| WO | WO 2009/085486 A1 | 7/2009 |

OTHER PUBLICATIONS

EP Search Report 14 16 2843.8-1659 dated Aug. 11, 2014.
U.S. Appl. No. 14/824,508, filed Aug. 12, 2015.
European Search Report dated Mar. 11, 2015 for corresponding EP 14190334.
European Search Report dated Jan. 12, 2017 for corresponding EP 16183699.4.
Examination Report for Australia Patent Application No. 2014201935, dated Feb. 21, 2018.
Examination Report for Europe Patent Application No. 14190334.4, dated Feb. 28, 2018.
Notification for Reasons of Refusal for Japan Patent Application No. 2014-080835, dated Jan. 30, 2018.
Office Action for U.S. Appl. No. 13/860,921, dated Oct. 3, 2017.
Office Action for U.S. Appl. No. 13/860,921, dated Feb. 26, 2016.
Office Action for U.S. Appl. No. 13/860,921, dated Mar. 23, 2017.
Office Action for U.S. Appl. No. 13/860,921, dated Sep. 13, 2016.
Examination Report for Australia Patent Application No. 2014201935, dated Jun. 14, 2017.
Office Action for China Patent Application No. 20144233.9, dated Oct. 25, 2017.
Examination Report for Australia Patent Application No. 2014248091, dated Jun. 26, 2018.
Office Action for China Patent Application No. 20144233.9, dated Jun. 11, 2018.
Examination Report for European Patent Application No. 14162843. 8, dated May 14, 2018.
Examination Report for European Patent Application No. 16183699. 4, dated Jun. 8, 2018.
Notification for Reasons of Refusal for Japan Patent Application No. 2014-080835, dated Jun. 26, 2018.
Notification for Reasons of Refusal for Japan Patent Application No. 2014-217009, dated Aug. 7, 2018.

* cited by examiner

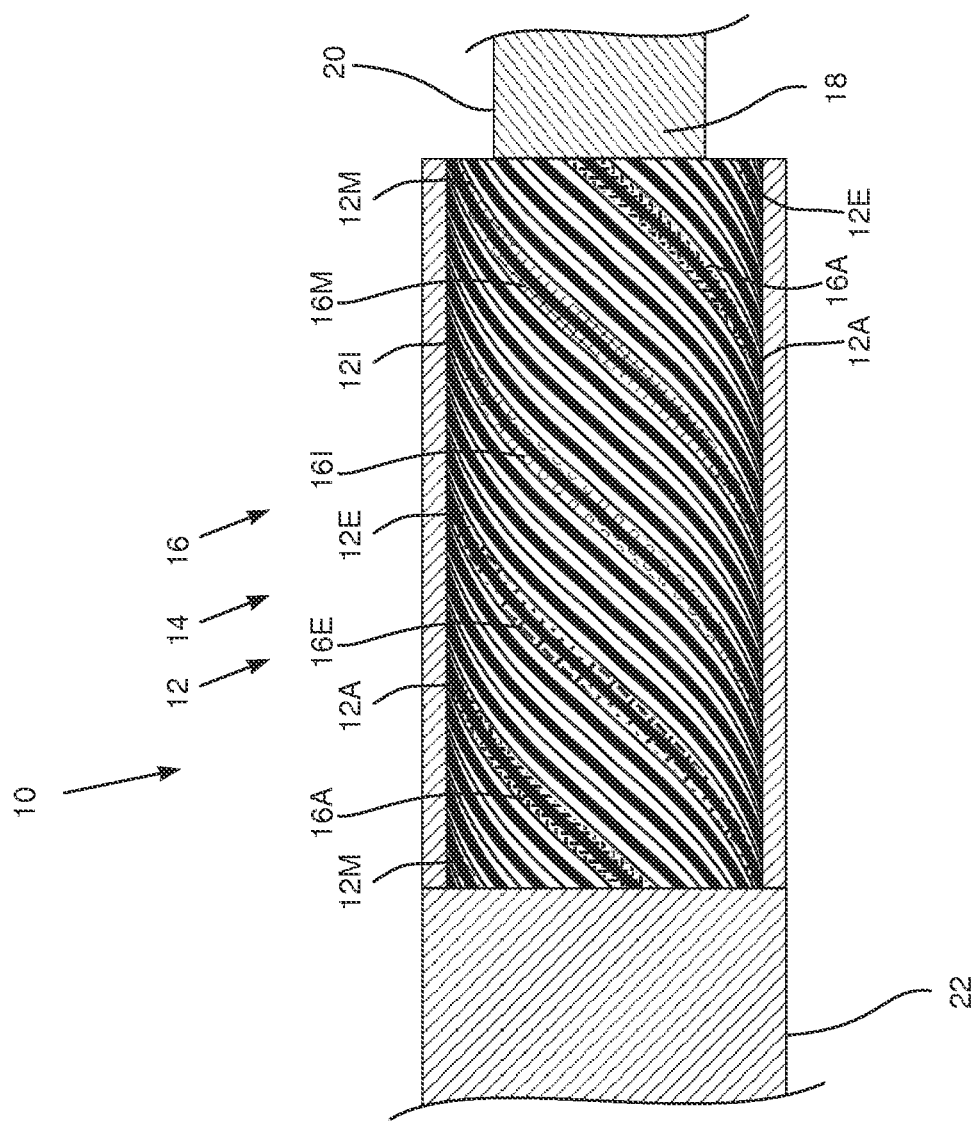
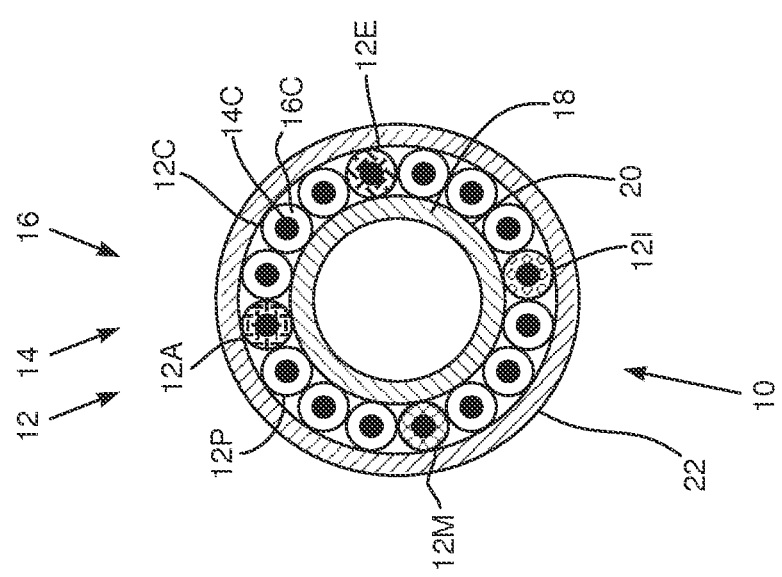
FIG. 1B
FIG. 1A

CONNECTION OF ELECTRODES TO WIRES COILED ON A CORE

CROSS-REFERENCE TO RELATED APPLICATION

This application is a continuation-in-part of U.S. patent application Ser. No. 13/860,921, entitled "High Density Electrode Structure," filed Apr. 11, 2013, which is incorporated herein by reference.

FIELD OF THE INVENTION

The present invention relates generally to cabling, and specifically to connection of an electrode to the cabling.

BACKGROUND OF THE INVENTION

U.S. Patent Application 2012/0172714, to Govari et al., whose disclosure is incorporated herein by reference, describes a method for incorporating a conducting wire into a tubular braid consisting of a multiplicity of supporting wires, and covering the tubular braid with a sheath. The method further includes identifying a location of the conducting wire within the tubular braid and attaching an electrode through the sheath to the conducting wire at the location.

U.S. Pat. No. 6,213,995, to Steen, et al., whose disclosure is incorporated herein by reference, describes a flexible tubing which includes a wall provided with a plurality of braided elements forming a braid within the wall of the tube. The braided elements are stated to include one or more signal transmitting elements and one or more metallic or non-metallic structural elements having structural properties different from the signal transmitting elements.

U.S. Pat. No. 7,229,437, to Johnson, et al., whose disclosure is incorporated herein by reference, describes a catheter having electrically conductive traces and external electrical contacts. The disclosure states that each trace may be in electrical connection with one or more external electrical contacts.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method for attaching an electrode to cabling, including:

providing a cable consisting of a plurality of insulated wires coiled around a central core;

removing insulation from each wire in a set of the coiled wires so as to provide a respective access channel to a respective section of a respective conductor of each wire in the set while the respective section remains coiled on the central core; and fastening a respective electrode to the respective access channel while the respective section remains coiled on the central core.

In a disclosed embodiment, the method further includes positioning a solder ball in proximity to the respective access channel prior to fastening the respective electrode, wherein fastening the respective electrode consists of melting the solder ball so that solidified solder connects the respective section of the respective conductor, via the respective access channel, to the respective electrode. Typically, positioning the solder ball includes applying glue over the respective access channel, and holding the solder ball in place with the glue.

In a further disclosed embodiment the respective electrode completely encircles the cabling. Alternatively, the respective electrode partially encircles the cabling.

In a yet further disclosed embodiment the wires are coiled single-handedly around the central core. Alternatively, the set includes a first group of the wires coiled left-handedly around the central core, and a second group of the wires coiled right-handedly around the central core.

Typically, the method includes using the cabling in an invasive medical procedure.

There is further provided, according to an embodiment of the present invention, apparatus, including:

a cable consisting of a plurality of insulated wires coiled around a central core;

a respective access channel to a respective section of a respective conductor of each wire in a set of the coiled wires, formed by removing insulation from each wire in the set while the respective section remains coiled on the central core; and a respective electrode fastened to the respective access channel while the respective section remains coiled on the central core.

The present disclosure will be more fully understood from the following detailed description of the embodiments thereof, taken together with the drawings, in which:

BRIEF DESCRIPTION OF THE DRAWINGS

FIGS. 1A and 1B are schematic views of cabling, according to an embodiment of the present invention;

DETAILED DESCRIPTION OF EMBODIMENTS

Overview

Figure 2A:
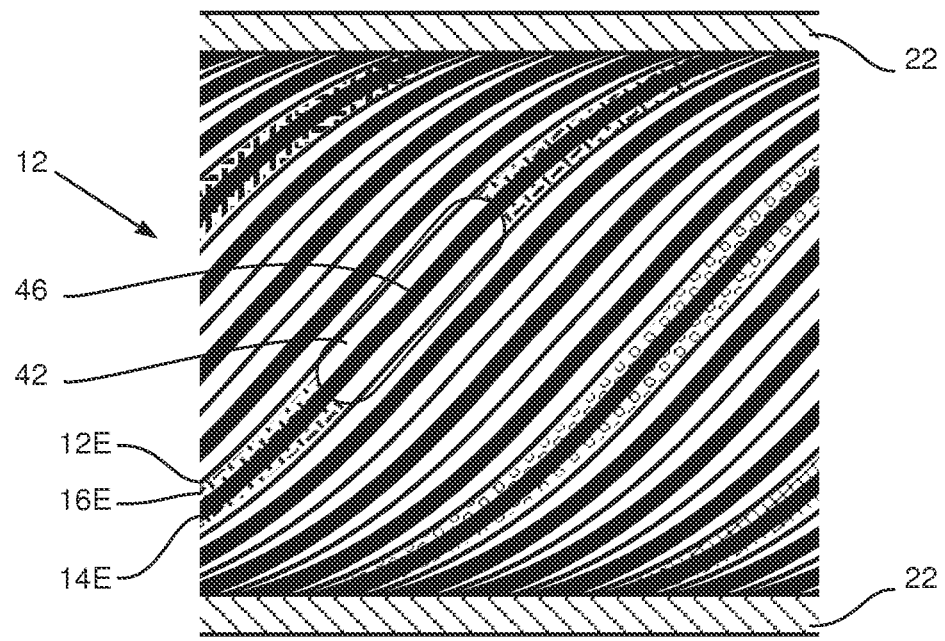
FIGS. 2A-2E are schematic diagrams illustrating steps in attaching an electrode to the cabling, according to embodiments of the present invention.

An embodiment of the present invention provides a method for attaching an electrode to cabling. The cabling comprises a cable having a plurality of insulated wires coiled around a central core. In order to attach the electrode to the cabling, insulation is removed from a section of a given wire, so as to provide an access channel to a corresponding section of a conductor in the given wire. The removal of the insulation is performed while the given wire remains coiled around the central core.

Once the access channel has been formed, the electrode may be fastened to it, while the given wire remains coiled around the central core.

Typically, prior to fastening the electrode, a solder ball is positioned in proximity to the access channel, and may be held in place by glue applied over the access channel. The electrode may then be placed over the solder ball. The fastening then includes electrically connecting the electrode to the conductor by melting, then cooling, the solder so that solidified solder connects the electrode and the corresponding section of the conductor via the access channel. The melting may be implemented by applying heat to the electrode.

System Description

Reference is now made to FIGS. 1A and 1B, which are schematic views of cabling 10, according to an embodiment of the present invention. FIG. 1A is a schematic cross-sectional view of the cabling. FIG. 1B is a schematic, side view of cabling 10, which has been partially cut-away to expose internal elements of the cabling. As is explained further below, an electrode is attached to the cabling, and the cabling is typically configured so that a large number of separate electrodes, each having respective attached wires, may be attached in a small length of the cabling, so that cabling 10 is capable of supporting a high density of electrodes. Cabling 10 is typically used as part of a medical catheter wherein electrical measurements are to be made from the electrodes attached to the cabling.

Cabling 10 comprises a plurality of generally similar wires 12, each wire 12 being formed as a conductor 14 covered by an insulating layer 16. In the following description, generally similar components associated with cabling 10 are referred to generically by their identifying component numeral, and are differentiated from each other, as necessary, by appending a letter A, B, . . . to the numeral. Thus wire 12C is formed as conductor 14C covered by insulating layer 16C. While embodiments of the present invention may be implemented with substantially any plurality of wires 12 in the cabling, for clarity and simplicity in the following description cabling 10 is assumed to comprise 16 wires 12A, . . . 12E, . . . 12I, . . . 12M, . . . 12P.

(For purposes of illustration, insulating layers 16 of wires 12 have been drawn as having approximately the same dimensions as conductors 14. In practice, the insulating layer is typically approximately one-tenth the diameter of the wire.)

In order to be used as part of a medical catheter, an outer diameter of cabling 10 is implemented to be as small as possible. In one embodiment, cabling 10 is approximately cylindrical with a length of approximately 2 m, and an outer diameter approximately equal to 0.5 mm.

Wires 12 may be formed with any diameter wire that is consistent with the outer diameter of cabling 10. In one embodiment wires 12 are formed of 48 AWG wire, corresponding to a wire diameter of approximately 30 microns. In some embodiments of the present invention the inventors have used, inter alia, monel, constantan, or copper for conductors 14. While copper has a higher electrical conductivity than monel or constantan, it may have a tendency to break during production of the cabling. Both monel and constantan enhance the strength of cabling 10, but in environments where magnetic properties of materials are significant, such as during a magnetic resonance imaging procedure or in a catheter using magnetic navigation, it may be preferable to use constantan for conductors 14.

While monel, constantan and copper are provided as examples of the material used for conductors 14, it will be understood that embodiments of the present invention are not limited to a particular type of material, and any other convenient electrically conducting material may be used. In some embodiments wires that neighbor each other may be selected to have dissimilar conductors, such as copper and constantan, so as to be available for forming a thermocouple junction.

Wires 12 are formed over an internal core 18, which is typically shaped as a cylindrical tube, and core 18 is also referred to herein as tube 18. The core material is typically selected to be a thermoplastic elastomer such as a polyether block amide (PEBA). In a disclosed embodiment core 18 is formed of 40D Pebax, produced by Arkema, Colombes, France. In the disclosed embodiment core 18, by way of example, is cylindrical with a wall thickness of approximately 13 microns, and an outer diameter of approximately 0.4 mm. Wires 12 are formed on an outer surface 20 of core 18 by coiling the wires around the tube. Thus, in the case that core 18 is cylindrical, each wire 12 on the outer surface is in the form of a helical coil. In contrast to a braid, all helical coils of wires 12 have the same handedness, i.e., all wires of the cabling are left-handed, or all wires of the cabling are right-handed. In the present disclosure and in the claims, cabling, wherein all the wires of the cabling that are coiled around an internal core of the cabling have the same handedness, is referred to as single-handed cabling. Also in the present disclosure and in the claims, cabling wherein the wires of the cabling comprise a first group of wires coiled left-handedly and a second group of wires coiled right-handedly, is referred to as braided cabling. Typically in braided cabling the number of wires in the first group equals the number in the second group.

Further details of a single-handed cabling generally similar to cabling 10 are provided in U.S. patent application Ser. No. 13/860,921, referenced above. An example of a braided cabling is provided in U.S. Patent Application 2012/0172714, referenced above.

For simplicity, the following description considers only single-handed cabling, as is exemplified by cabling 10. However, embodiments of the present invention apply to either single-handed or braided cabling, and those having ordinary skill in the art will be able to adapt the description, mutatis mutandis, for braided cabling.

In coiling wires 12 on surface 20, the wires are typically arranged so that they contact each other in a "close-packed" configuration. In other words, if internal tube 18 were to be opened so that surface 20 is a flat plane, the wires (neglecting "end-effects") form a single wire layer over surface 20, with insulating layers 16 continuously in contact with two other insulating layers, and with the insulating layers being continuously in contact with surface 20.

In the case of tube 18 being cylindrical, the close-packed arrangement of the helical coils of wires 12 means that the wires are configured in a multi-start thread configuration. Such a configuration is described in more detail in U.S. patent application Ser. No. 13/860,921 referenced above.

Once wires 12 have been formed in the multi-start thread configuration described above, the wires are covered with a protective sheath 22. The protective sheath material is typically selected to be a thermoplastic elastomer such as PEBA. In a disclosed embodiment sheath 22 is formed of 55D Pebax, produced by Arkema, and no additives are incorporated in the sheath, so that it is transparent. In the disclosed embodiment sheath 22, by way of example, has an outer diameter of approximately 0.5 mm.

Typically, although not necessarily, the insulating layer of at least one of wires 12 is colored differently from the colors of the remaining wires. Such coloration aids in identifying particular wires once they have been arranged within cabling 10, assuming that sheath 22 is transparent. An alternative method for identifying particular wires in a braided arrangement is described in U.S. Patent Application 2012/0172714.

By way of example, in the embodiment described herein, using 16 wires, every fourth wire has its insulating layer colored, so that insulating layers 16A, 16E, 16I, and 16M are respectively colored green, black, red, and violet. The insulating layers of the remaining wires may be given another color, such as white, or may be left colorless. Thus, wires 12A, 12E, 12I, and 12M appear to have the colors green, black, red, and violet, and are visually different in appearance from the remaining wires.

The process of coiling wires 12 around a core, and then covering the wires by a sheath, essentially embeds the wires within a wall of cabling 10, the wall consisting of the core and the sheath. Embedding the wires within a wall means that the wires are not subject to mechanical damage when the cabling is used to form a catheter. Mechanical damage is prevalent for small wires, such as the 48 AWG wires exemplified above, if the wires are left loose during assembly of a catheter.

Figure 2B:
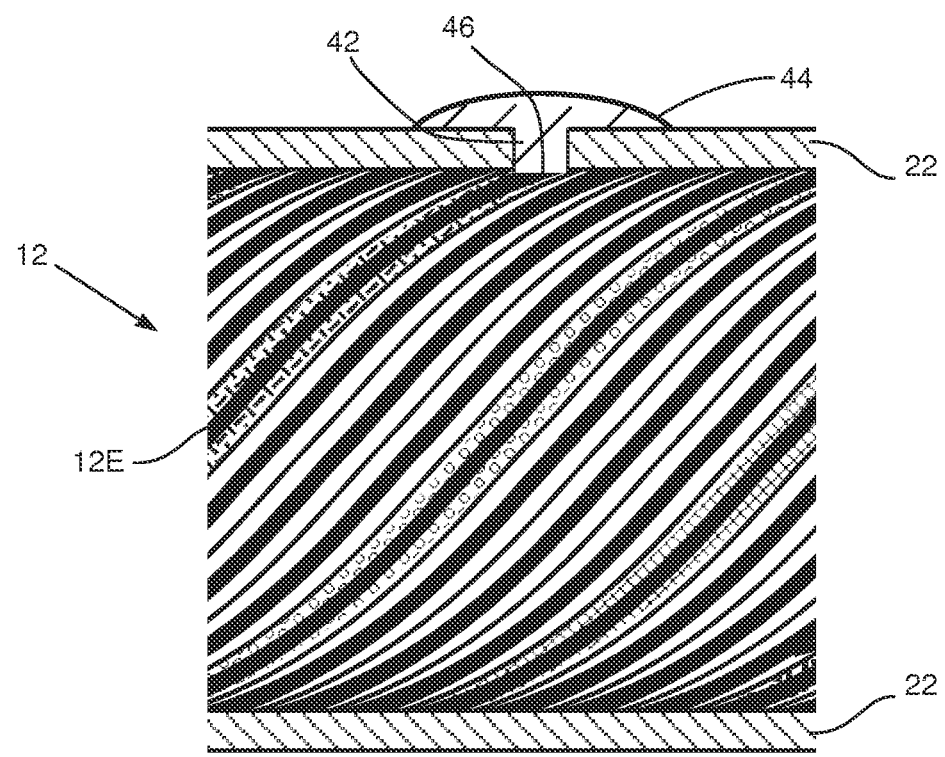
Figure 2C:
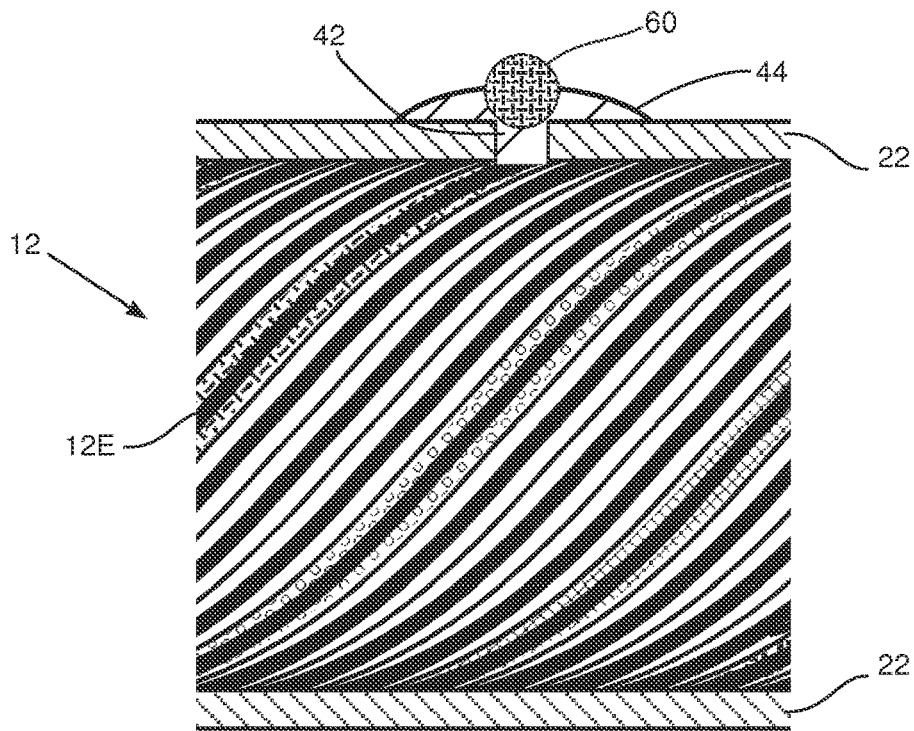
Figure 2D:
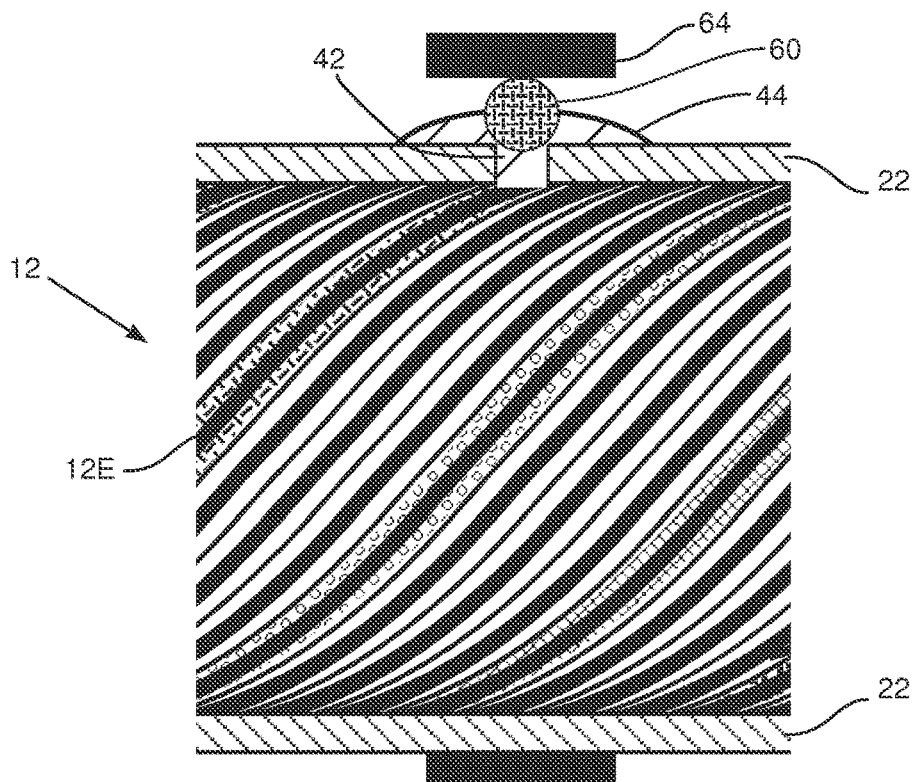
Figure 2E:
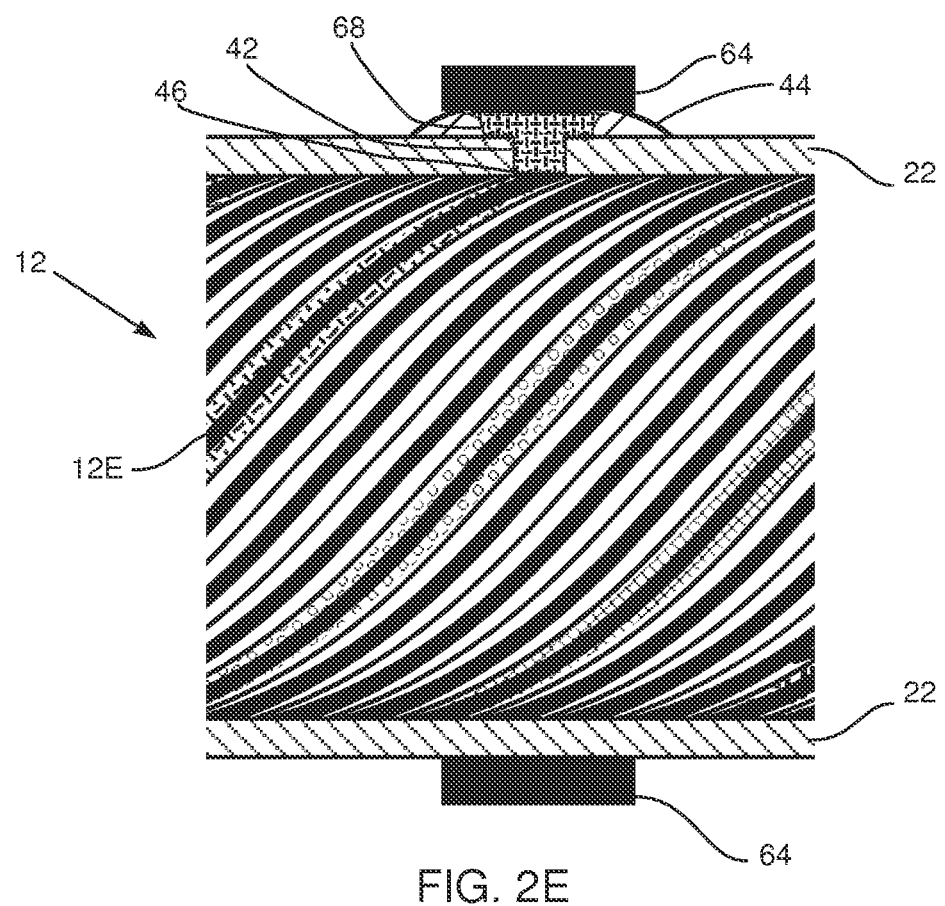
Figure 3:
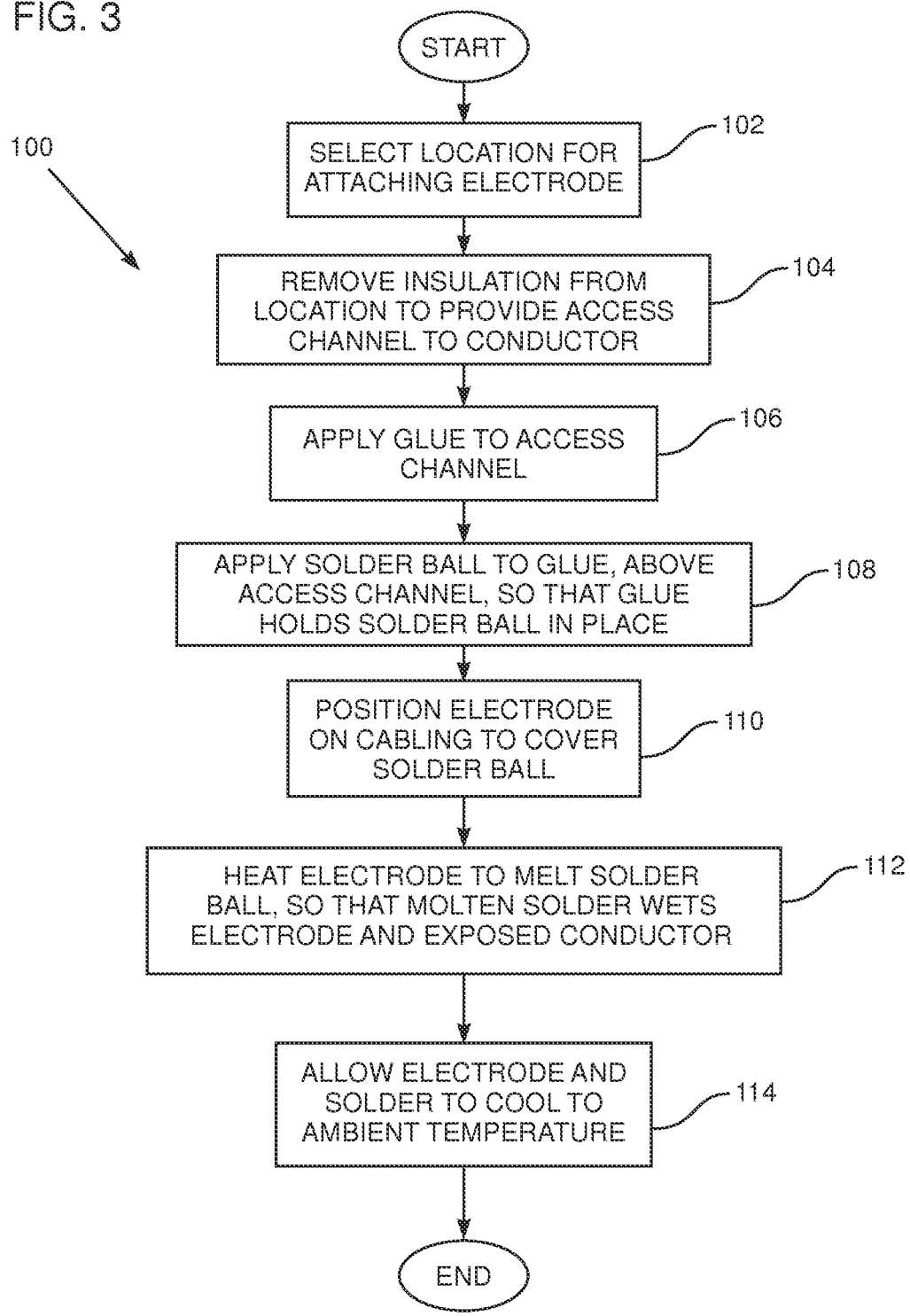
FIG. 3 is a flowchart describing the steps, according to an embodiment of the present invention.

FIGS. 2A-2E are schematic diagrams illustrating steps in attaching electrodes 64 to cabling 10, and FIG. 3 is a flowchart 100 describing the steps, according to embodiments of the present invention. Typically, up to 16 electrodes 64, i.e., electrodes 64A, 64B, . . . 64O, 64P, may be attached to respective wires of the cabling. The following description refers to a specific electrode by the generic term electrode 64.

FIG. 2A is a schematic top view of the cabling and FIGS. 2B-2E are schematic side views of the cabling in different stages of the attachment of electrode 64. In all views parts of sheath 22 have been cut-away to expose wires 12 of cabling 10, as well as to illustrate the attachment of electrode 64 to the cabling.

Electrode 64 is typically in the form of a conductive ring with dimensions enabling it to be slid over sheath 22. More details of alternative shapes for electrode 64 are provided below. The following explanation assumes that the electrode is to be attached to conductor 14E of colored wire 12E at a distal end of cabling 10.

In an initial step 102 a location for attaching the electrode is selected by first finding colored wire 12E visually, and then finding a required location for the electrode along the cabling. The visual determination is possible since sheath 22 is transparent.

In an access step 104 a section of sheath 22 above the wire, and a corresponding section of insulating layer 16E, are removed. The removal provides an access channel 42, through the insulation of sheath 22 and also through the insulation of layer 16E, to a section 46 of conductor 14E, as is illustrated in FIG. 2A. The removal of the insulation, which exposes the section of conductor 14E, may be by any convenient means, such as by using a laser to penetrate the insulation, or by mechanical removal of the insulation.

In a glue application step 106, glue 44 is applied over the access channel. The application of the glue typically covers channel 42, as is illustrated in FIG. 2B.

In a solder ball step 108, a solder ball 60 is positioned in proximity to the entrance of access channel 42, and is held in place relative to the channel by glue 44. The positioning of the solder ball is illustrated in FIG. 2C.

Typically, solder ball 60 is formed from a low melting point metal, or a low melting point alloy. In one embodiment of the present invention, solder ball 60 is formed from indium.

In an electrode positioning step 110, electrode 64 is located to be in contact with the solder ball. By way of example electrode 64 is assumed to be in the form of a ring, and is also referred to herein as ring electrode 64. In some embodiments ring electrode 64 completely encircles cabling 10, in which case the positioning of ring electrode 64 may be implemented by sliding the ring along cabling 10 so that the ring covers the solder ball. In alternative embodiments ring electrode 64 partially encircles cabling 10, as a "broken" ring, in which case the positioning of ring electrode 64 may be implemented by pushing the ring over cabling 10 so that the ring covers the solder ball. In the remaining description of the flowchart, ring electrode 64 is assumed to completely encircle the cabling. The positioning of ring electrode 64, for a completely encircling ring, to cover the solder ball is illustrated in FIG. 2D.

In a heating step 112 ring electrode 64 is heated, and while being heated is pressed onto ball 60. The combination of heat and pressure melts the solder of the ball so that the ball deforms, and so that the molten solder wets the inner surface of ring electrode 64 and also penetrates channel 42. The molten solder penetrating the channel wets the exposed section of conductor 14E.

In a final step 114, the heating applied to the ring electrode is removed, and the electrode and solder are allowed to cool, typically to ambient room temperature. On cooling, the solder solidifies into a solid solder bridge 68, as is illustrated in FIG. 2E. Bridge 68, which corresponds to a deformed solder ball, connects electrode 64 and section 46 of conductor 14E.

Figure 4:
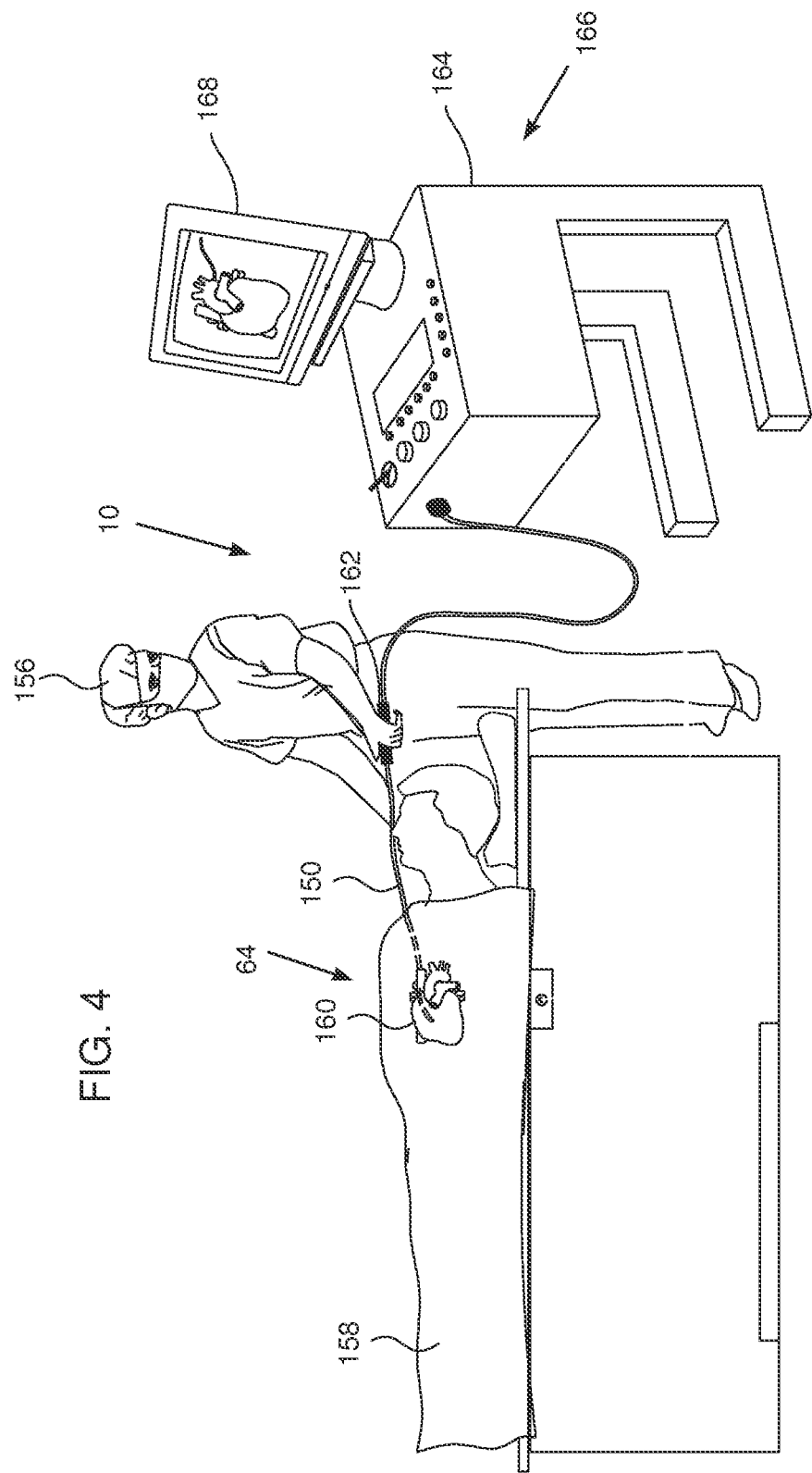
FIG. 4 is a schematic illustration of an invasive medical procedure using the cabling, according to an embodiment of the present invention.

FIG. 4 is a schematic illustration of an invasive medical procedure using cabling 10, according to an embodiment of the present invention. In preparation for the procedure, cabling 10 is incorporated into a catheter 150, the cabling having electrodes 64 at its distal end. Catheter 150 uses one set of cabling 10, and is typically a catheter that is used for measuring electrical properties of a body cavity. At its distal end catheter 150 may be straight or curved as a lasso or helical catheter.

By way of example, a medical professional 156 is assumed to insert catheter 150 into a patient 158 in order to acquire electropotential signals from a heart 160 of the patient. The professional uses a handle 162 attached to the catheter in order to perform the insertion, and signals generated at electrodes 64 are conveyed to a console 164.

Console 164 comprises a processing unit 166 which analyzes the received signals, and which may present results of the analysis on a display 168 attached to the console. The results are typically in the form of a map, numerical displays, and/or graphs derived from the signals.

A more detailed description of the use of a catheter such as catheter 150 in acquiring electropotentials is provided in U.S. Pat. Nos. 6,584,345 and 6,400,981, both to Govari, which are incorporated herein by reference.

While the description above has been generally directed to attaching an electrode to cabling having wires coiled in a single-handed manner, it will be appreciated that the scope of the present invention includes cabling that is braided, i.e., wherein the cabling comprises wires formed as both left- and right-handed coils. It will also be appreciated that the electrode attached to the cabling need not be in the form of a ring encircling the cabling, but rather may be any convenient shape that does not encircle the cabling.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. An apparatus, comprising:
   a cable comprising a plurality of insulated wires coiled around a central core in a close-packed configuration, each of the insulated wires having a respective conductor surrounded by insulation;
   an access channel to at least one conductor of at least one insulated wire in the cable, formed by removing a portion of the insulation from the at least one insulated wire while the cable remains coiled on the central core; and
   a ring electrode having an inner surface connected by a deformed solder ball to the at least one conductor of the at least one insulated wire via the respective access channel, the connection between the inner surface of the ring electrode and the at least one conductor being formed by heating the ring electrode while pressing the ring electrode onto an undeformed solder ball, wherein the undeformed solder ball is positioned prior to deformation in proximity to an entrance of the access channel such that the undeformed solder ball is not electrically coupled with the conductor of the at least one insulated wire, wherein the heating and pressing melt and deform the undeformed solder ball such that the solder ball subsequently penetrates the access channel forming a bridge and when cooled, the deformed solder ball bridge connects and electrically couples the ring electrode to the conductor of the at least one insulated wire via the access channel.

2. The apparatus according to claim 1 further comprising glue, applied over the access channel, that holds the undeformed solder ball in place.

3. The apparatus according to claim 1, wherein the electrode completely encircles the cable.

4. The apparatus according to claim 1, wherein the electrode partially encircles the cable.

5. The apparatus according to claim 1, wherein the wires are coiled single-handedly around the central core.

6. The apparatus according to claim 1, wherein the cable comprises a first group of the wires coiled left-handedly around the central core, and a second group of the wires coiled right-handedly around the central core.

7. A method for attaching an electrode to cable, comprising:
   providing the cable having a plurality of insulated wires coiled around a central core in a close-packed configuration, each of the insulated wires having a respective conductor surrounded by insulation;
   removing a portion of the insulation from at least one of the insulated wires in the cable so as to provide an access channel to the conductor of the at least one insulated wire while the cable remains coiled on the central core;
   positioning an undeformed solder ball in proximity to an entrance of the access channel such that the undeformed solder ball is not electrically coupled with the conductor of the at least one insulated wire;
   positioning a ring electrode in contact with the undeformed solder ball; and
   heating the ring electrode while pressing the ring electrode onto the undeformed solder ball to melt and deform the solder ball such that the solder ball subsequently penetrates the access channel forming a bridge and when cooled, the deformed solder ball bridge connects and electrically couples an inner surface of the ring electrode to the conductor of the at least one insulated wire via the access channel.

8. The method according to claim 7, wherein positioning the undeformed solder ball comprises applying glue over the access channel, and holding the undeformed solder ball in place with the glue.

9. The method according to claim 7, wherein the electrode completely encircles the cable.

10. The method according to claim 7, wherein the electrode partially encircles the cabling.

11. The method according to claim 7, wherein the wires are coiled single-handedly around the central core.

12. The method according to claim 7, wherein the cable comprises a first group of the wires coiled left-handedly around the central core, and a second group of the wires coiled right-handedly around the central core.

\* \* \* \* \*